US012496401B2

(12) United States Patent
Walsh et al.

(10) Patent No.: US 12,496,401 B2
(45) Date of Patent: Dec. 16, 2025

(54) MINIATURIZED WEARABLE MEDICATION ADMINISTRATION DEVICE

(71) Applicant: RX BANDZ, INC., Locust Valley, NY (US)

(72) Inventors: Jessica Walsh, Upper Brookville, NY (US); John Dinesen, Austin, TX (US); Stephen Harhen, Austin, TX (US)

(73) Assignee: RX BANDZ, INC., Locust Valley, NY (US)

( * ) Notice: Subject to any disclaimer, the term of this patent is extended or adjusted under 35 U.S.C. 154(b) by 1144 days.

(21) Appl. No.: 17/203,728

(22) PCT Filed: Sep. 17, 2019

(86) PCT No.: PCT/US2019/051589
§ 371 (c)(1),
(2) Date: Mar. 16, 2021

(87) PCT Pub. No.: WO2020/061100
PCT Pub. Date: Mar. 26, 2020

(65) Prior Publication Data

US 2021/0386932 A1 Dec. 16, 2021

Related U.S. Application Data

(60) Provisional application No. 62/732,442, filed on Sep. 17, 2018.

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/2053* (2013.01); *A61M 5/31543* (2013.01);
(Continued)

(58) Field of Classification Search
CPC .......... A61M 2005/206; A61M 5/2033; A61M 5/14248; A61M 5/20; A61M 5/24;
(Continued)

(56) References Cited

U.S. PATENT DOCUMENTS 3,093,242 A 6/1963 Huyck et al.
3,393,833 A 7/1968 King
(Continued)

FOREIGN PATENT DOCUMENTS

CN 102655897 A 9/2012
WO WO-9813077 A2 4/1998
(Continued)

OTHER PUBLICATIONS

Canadian Office Action for Canadian Application No. 3113230, dated Jun. 1, 2022, 3 pages.
(Continued)

*Primary Examiner* — Loan B Jimenez
*Assistant Examiner* — Kathleen Paige Farrell
(74) *Attorney, Agent, or Firm* — Jacob M. Ward; Ward Law Office LLC

(57) ABSTRACT

A device includes a housing having a first end, a second end, a first cylinder, a second cylinder parallel to the first cylinder, and a channel connecting the first and second cylinders near the second end. A piston is positioned within the first cylinder. A cartridge containing a therapeutic agent is positioned within the second cylinder. A needle hub containing a needle is positioned within the second cylinder between the cartridge and the first end. A septum is positioned at the first end. A fluid is positioned within the first cylinder. When the device is activated, the piston travels toward the second end, forcing some of the fluid to travel from the first cylinder into the second cylinder, forcing the cartridge toward the first end, causing the needle to penetrate the cartridge and
(Continued)

the septum, and causing at least some of the therapeutic agent to extrude through the needle.

20 Claims, 10 Drawing Sheets

(52) U.S. Cl.
CPC ........ *A61M 5/3158* (2013.01); *A61M 5/3202* (2013.01); *A61M 2005/2013* (2013.01); *A61M 5/3234* (2013.01); *A61M 2205/3327* (2013.01); *A61M 2209/088* (2013.01)

(58) Field of Classification Search
CPC .......... A61M 2005/14252; A61M 5/19; A61M 2005/14506; A61M 5/1454; A61M 5/2053; A61M 5/1452; A61M 5/14526; A61M 2005/2013; A61M 5/31543; A61M 5/3158; A61M 5/3202; A61M 5/3234; A61M 2205/3327; A61M 2209/088; A61M 5/5086; A61M 2005/2073; A61M 2005/247; A61M 2005/31518; A61M 2205/273
See application file for complete search history.

(56) References Cited

U.S. PATENT DOCUMENTS

| | | | | |
|---|---|---|---|---|
| 3,910,260 | A | 10/1975 | Sarnoff et al. | |
| 3,941,130 | A | 3/1976 | Tibbs | |
| 4,004,577 | A | 1/1977 | Sarnoff | |
| 4,178,928 | A | 12/1979 | Tischlinger | |
| 4,261,358 | A | 4/1981 | Vargas et al. | |
| 4,525,164 | A | 6/1985 | Loeb et al. | |
| 4,685,902 | A | 8/1987 | Edwards et al. | |
| 4,689,042 | A | 8/1987 | Sarnoff et al. | |
| 4,755,169 | A | 7/1988 | Sarnoff et al. | |
| 4,768,688 | A | 9/1988 | Harrigan | |
| 4,795,433 | A | 1/1989 | Sarnoff | |
| 4,865,590 | A | 9/1989 | Marmar | |
| 4,921,277 | A | 5/1990 | Mcdonough | |
| 5,024,656 | A | 6/1991 | Gasaway et al. | |
| 5,064,413 | A | 11/1991 | Mckinnon et al. | |
| 5,085,642 | A | 2/1992 | Sarnoff et al. | |
| 5,092,843 | A | 3/1992 | Monroe et al. | |
| 5,102,393 | A | 4/1992 | Sarnoff et al. | |
| 5,135,479 | A | 8/1992 | Sibalis et al. | |
| 5,217,143 | A | 6/1993 | Aitken | |
| 5,267,963 | A | 12/1993 | Bachynsky | |
| 5,536,249 | A | 7/1996 | Castellano et al. | |
| 5,658,259 | A | 8/1997 | Pearson et al. | |
| 6,149,626 | A | 11/2000 | Bachynsky et al. | |
| 6,270,479 | B1 | 8/2001 | Bergens et al. | |
| 6,371,939 | B2 | 4/2002 | Bergens et al. | |
| 6,800,070 | B2 | 10/2004 | Mazidji et al. | |
| 6,926,699 | B2 | 8/2005 | Stone | |
| 8,109,912 | B2 | 2/2012 | Alferness et al. | |
| 8,409,141 | B2 | 4/2013 | Johansen et al. | |
| 8,876,779 | B2 | 11/2014 | Johansen et al. | |
| 8,956,331 | B2 | 2/2015 | Johansen et al. | |
| 9,084,849 | B2 | 7/2015 | Edwards et al. | |
| 9,101,706 | B2 | 8/2015 | Gonnelli et al. | |
| 9,173,999 | B2 | 11/2015 | Edwards et al. | |
| 9,474,862 | B2 | 10/2016 | Walsh | |
| 9,636,460 | B1 * | 5/2017 | Jaeger | A61M 5/31591 |
| 2002/0007154 | A1 | 1/2002 | Hansen et al. | |
| 2005/0273054 | A1 | 12/2005 | Asch | |
| 2006/0178638 | A1 * | 8/2006 | Reynolds | A61M 5/31511 |
| 2008/0132840 | A1 | 6/2008 | Kirchhofer | |
| 2008/0183140 | A1 * | 7/2008 | Paproski et al. | A61M 5/326 |
| 2009/0099521 | A1 | 4/2009 | Gravesen et al. | |
| 2009/0259176 | A1 * | 10/2009 | Yairi | A61M 35/10 604/290 |
| 2010/0094254 | A1 | 4/2010 | Casey et al. | |
| 2011/0306929 | A1 * | 12/2011 | Levesque et al. | A61M 5/14248 |
| 2012/0209183 | A1 * | 8/2012 | Gray | F04B 7/00 604/131 |
| 2013/0023822 | A1 | 1/2013 | Edwards et al. | |
| 2013/0023825 | A1 | 1/2013 | Edwards et al. | |
| 2013/0046239 | A1 | 2/2013 | Gonnelli et al. | |
| 2013/0060196 | A1 | 3/2013 | O'Connor et al. | |
| 2013/0079747 | A1 | 3/2013 | Gross et al. | |
| 2014/0200510 | A1 | 7/2014 | Agard et al. | |
| 2014/0296787 | A1 | 10/2014 | Agard et al. | |
| 2015/0011976 | A1 * | 1/2015 | Vouillamoz | A61M 5/14248 604/506 |
| 2015/0141920 | A1 | 5/2015 | O'Connor et al. | |
| 2015/0306306 | A1 | 10/2015 | Gonnelli et al. | |
| 2016/0045670 | A1 | 2/2016 | Edwards et al. | |
| 2016/0158462 | A1 | 6/2016 | Schoonmaker et al. | |
| 2016/0184521 | A1 | 6/2016 | Edwards et al. | |
| 2017/0021104 | A1 | 1/2017 | Walsh | |
| 2017/0136183 | A1 * | 5/2017 | Helmer | A61M 5/347 |
| 2017/0182242 | A1 * | 6/2017 | Galitz | A61M 5/20 |
| 2017/0232207 | A1 | 8/2017 | Zivkovic et al. | |
| 2017/0246393 | A1 * | 8/2017 | Genosar | A61M 39/22 |
| 2017/0361016 | A1 | 12/2017 | Levesque et al. | |
| 2018/0064881 | A1 * | 3/2018 | Whalley | A61M 5/16886 |
| 2018/0110925 | A1 | 4/2018 | Rioux et al. | |
| 2018/0193557 | A1 | 7/2018 | Johnson et al. | |
| 2018/0304017 | A1 | 10/2018 | Edwards et al. | |
| 2019/0307955 | A1 | 10/2019 | Levesque et al. | |
| 2020/0086051 | A1 * | 3/2020 | Grygus | A61M 5/2033 |
| 2020/0139107 | A1 | 5/2020 | Masterson et al. | |
| 2020/0164155 | A1 * | 5/2020 | Mojarrad | A61M 5/3202 |

FOREIGN PATENT DOCUMENTS

| | | | |
|---|---|---|---|
| WO | WO-0183008 | A1 | 11/2001 |
| WO | WO-2008005315 | A2 | 1/2008 |
| WO | WO-2009070605 | A1 | 6/2009 |
| WO | WO-2010089589 | A1 | 8/2010 |
| WO | WO-2011021098 | A1 | 2/2011 |
| WO | WO-2011046950 | A1 | 4/2011 |
| WO | WO-2012090186 | A1 | 7/2012 |
| WO | WO-2013019939 | A2 | 2/2013 |
| WO | WO-2013034986 | A2 | 3/2013 |
| WO | WO-2014063112 | A1 | 4/2014 |
| WO | WO-2016009165 | A1 | 1/2016 |
| WO | WO-2016091978 | A1 | 6/2016 |
| WO | WO-2020061100 | A1 | 3/2020 |
| WO | WO-2023141627 | A2 | 7/2023 |

OTHER PUBLICATIONS

Extended European Search Report for European Application No. EP20190861483 dated Jul. 26, 2022, 8 Pages.
International Preliminary Report on Patentability for International Application No. PCT/US2013/070438, dated May 17, 2016, 6 pages.
International Preliminary Report on Patentability for International Application No. PCT/US2019/051589, dated Mar. 9, 2021, 5 pages.
International Search Report and Written Opinion International Application No. PCT/US2013/070438, mailed Aug. 14, 2014, 8 pages.
International Search Report and Written Opinion International Application No. PCT/US2019/051589, mailed Dec. 4, 2019, 7 pages.
How V-Go Works' (V-GO Simple Insulin Patch) Dec. 7, 2017 (online) retrieved from <URL: https://www.youtube.com/watch?time_continue=158&v=Oupic7ts-mw> entire document, especially figs. 1-8: timestamp 0:40-2:00.

* cited by examiner

MINIATURIZED WEARABLE MEDICATION ADMINISTRATION DEVICE

CROSS-REFERENCE TO RELATED APPLICATION

This application is an international (PCT) application relating to and claiming the benefit of commonly-owned, co-pending U.S. Provisional Patent Application No. 62/732,442, titled "MINIATURIZED WEARABLE MEDICATION ADMINISTRATION DEVICE," having a filing date of Sep. 17, 2018, which is incorporated by reference herein in its entirety.

FIELD OF THE INVENTION

The field of invention relates to a wearable device for administration of medication to a subject in need thereof. In particular, the field of invention relates to a miniaturized needle-based autoinjector.

BACKGROUND OF THE INVENTION

Devices have been used to administer medications under emergency conditions, such as, for example, administering epinephrine to counteract the effects of a severe allergic reaction (e.g., anaphylaxis) or naloxone for opioid overdose. Devices have also been described for use in administering medications to treat disease, such as, for example, anti-arrhythmic medications and selective thrombolytic agents during a heart attack. Autoinjectors offer an alternative to manually operated syringes for administering therapeutic agents into subjects in need thereof, or allowing subjects in need thereof to self-administer medications. Frequently, autoinjectors administer medication to the subject via injection.

Current autoinjectors are frequently cumbersome and may not be readily accessible, or easily carried by the user. In particular, due to the bulk of the current autoinjectors, the devices tend to be carried in the subject's bag, or back pack, or purse, or car, not on the subject's person. In addition, the currently available autoinjectors have a number of problems in form, function, and appeal. These problems can contribute to incorrect use, misuse, not carrying the unit as prescribed (non-compliance), and can result in an adverse outcome including death. By way of example, anaphylaxis is a severe medical emergency that if not treated quickly and appropriately can be fatal. It occurs unexpectedly and may progress rapidly in patients of all ages, but most often in the young and otherwise healthy. One common cause of anaphylaxis is food allergy, especially to peanuts, which is increasing in prevalence. Other causes exist, such as, for example, other food allergens, adverse reactions to medications, or adverse reactions to insect bites or stings. Rapid diagnosis is essential and immediate injection of intramuscular epinephrine is the treatment of choice, the response to which is often dramatic and potentially life-saving. The early injection of epinephrine is the most important factor in anaphylaxis outcome. People who survive near fatal anaphylactic reactions receive intramuscular injections promptly while those who die do not.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY OF THE INVENTION

Figure 1:
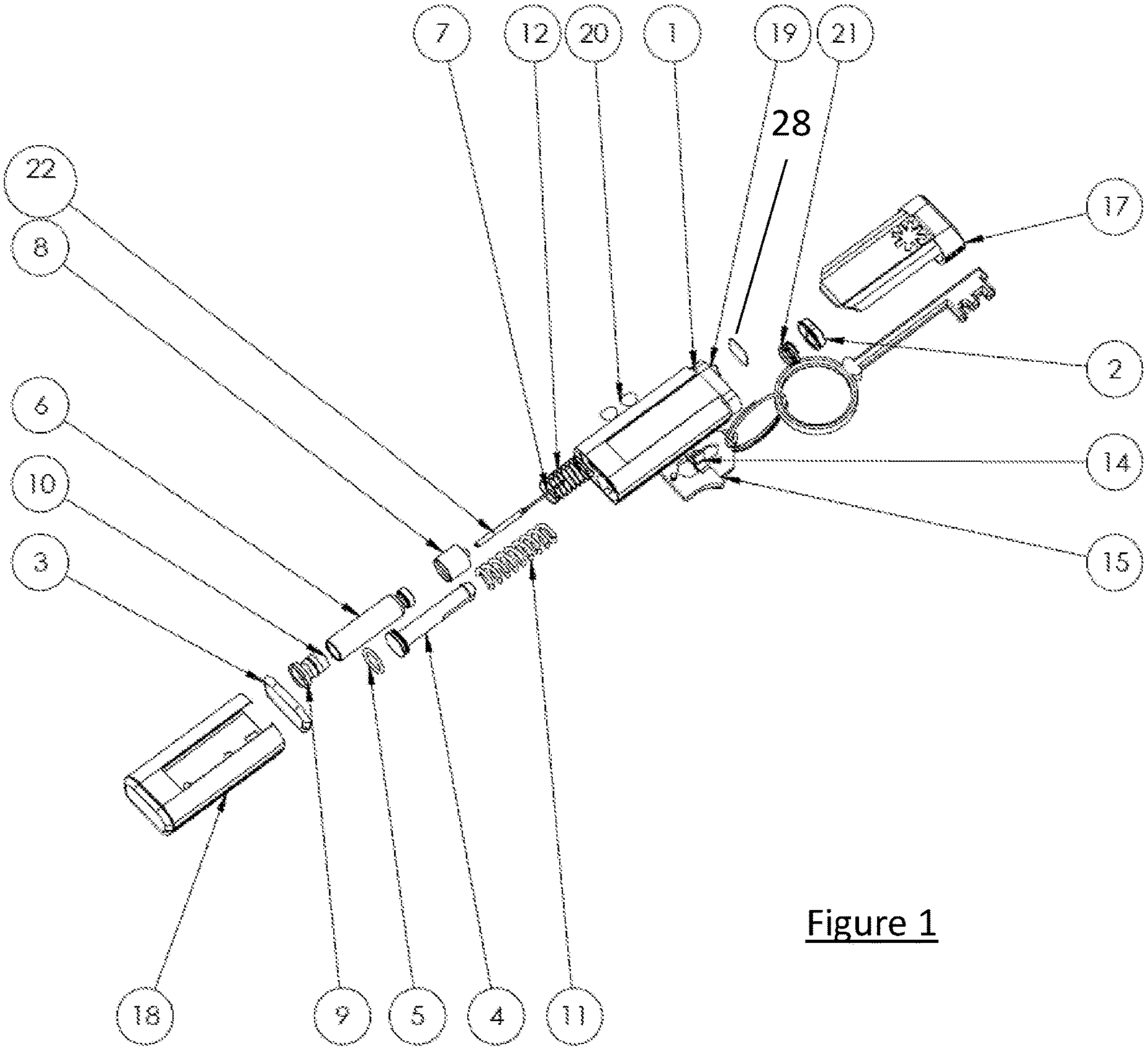
FIG. 1 shows an exploded perspective view of an exemplary miniaturized wearable medication administration device.

In an embodiment, a device includes a housing having a first end, a second end, a first cylinder, a second cylinder, a channel connecting the first cylinder to the second cylinder proximate the second end, a piston slidably positioned within the first cylinder, a spring configured to force the piston toward the second end of the housing, an activation trigger positioned on the first end of the housing and configured to retain the piston proximate the first end of the housing prior to activation and to allow the piston to move along the first cylinder upon activation, a penetrable septum positioned on the first end of the housing adjacent to the activation trigger, a cartridge having a first end and a second end, the cartridge containing a therapeutic agent, the cartridge being positioned within the second cylinder such that the first end of the cartridge faces the first end of the housing and the second end of the cartridge faces the second end of the housing, the cartridge having a plunger at the second end thereof, a cartridge sealing ring positioned adjacent the second end of the cartridge, a needle hub positioned adjacent the first end of the cartridge and within the second cylinder such that the cartridge is positioned within the needle hub a dual-ended needle positioned within the needle hub, a retraction spring positioned within the second cylinder and configured to force the needle hub toward the second end of the cylinder, and a fluid positioned within the first cylinder, the channel, and the second cylinder, whereby, when the piston travels along the first cylinder toward the second end of the housing, the piston drives some of the fluid through the channel into the second cylinder, thereby driving the cartridge sealing ring, the cylinder, the needle hub, and the needle toward the first end of the housing, thereby causing the needle to penetrate the septum and subsequently to penetrate the cartridge, wherein continued travel of the fluid causes the plunger to move within the cartridge and extrude at least some of the therapeutic agent through the needle, wherein the first cylinder includes a relief bore positioned proximate the second end of the housing, the relief bore configured such that, when a head of the piston is positioned between the relief bore and the second end of the housing, the fluid is permitted to flow into a portion of the first cylinder between the head of the piston and the first end of the housing, thereby removing pressure from the cartridge sealing ring, and wherein the retraction spring is configured to force the needle hub toward the second end of the housing when pressure is removed from the cartridge sealing ring, thereby causing corresponding motion of the needle toward the second end of the housing and retracting the needle so as to be positioned entirely within the housing.

In an embodiment, a device includes a housing having a first end, a second end, a first cylinder, a second cylinder parallel to the first cylinder, and a channel connecting the first cylinder to the second cylinder proximate to the second end; a piston slidably positioned within the first cylinder; a deployment spring configured to force the piston toward the second end of the housing; an activation trigger positioned proximate to the first end of the housing, wherein the activation trigger is configured to retain the piston proximate the first end of the housing prior to actuation of the activation trigger, and wherein the activation trigger is configured to release the piston and to allow the piston to move along the first cylinder upon actuation of the activation trigger; a penetrable septum positioned at the first end of the housing proximate to the activation trigger, wherein the penetrable septum separates an interior of the housing from an external environment surrounding the housing; a cartridge having a first end and a second end, wherein the cartridge contains at least one therapeutic agent, wherein the cartridge is positioned within the second cylinder such that the first end of the cartridge faces the first end of the housing and the second end of the cartridge faces the second end of the housing, and wherein the cartridge has a plunger at the second end thereof; a needle hub positioned adjacent to the first end of the cartridge and within the second cylinder, wherein the cartridge is slidably positioned within the needle hub; a dual-ended needle positioned within the needle hub; and a fluid positioned within the first cylinder, the channel, and the second cylinder, wherein the piston is configured such that, when the activation trigger is actuated, the activation trigger releases the piston and the deployment spring causes the piston to travel along the first cylinder toward the second end of the housing, thereby driving at least some of the fluid through the channel into the second cylinder, thereby driving the cartridge, the needle hub, and the needle toward the first end of the housing, and thereby causing the needle to penetrate the septum and subsequently to penetrate the cartridge; and wherein the plunger is configured such that continued travel of the fluid causes the plunger to move within the cartridge and force at least some of the at least one therapeutic agent to extrude through the needle.

In an embodiment, the device also includes a retraction spring positioned within the second cylinder, wherein the retraction spring is configured to force the needle hub toward the second end of the cylinder. In an embodiment, the piston includes a piston head, the first cylinder includes a relief bore positioned proximate to the second end of the housing, the relief bore is configured such that, when the piston head is positioned between the relief bore and the second end of the housing, the fluid is permitted to flow into a portion of the first cylinder between the head of the piston and the first end of the housing, thereby removing pressure from the cartridge sealing ring, and the retraction spring is configured to force the needle hub toward the second end of the housing when pressure is removed from the cartridge sealing ring, thereby causing corresponding motion of the needle toward the second end of the housing and retraction of the needle so as to be positioned entirely within the housing. In an embodiment, a position of the relief bore is configured so as to control an amount of the at least one therapeutic agent to be extruded through the needle. In an embodiment, the deployment spring and the retraction spring are configured such that an elapsed time between an actuation of the activation trigger and a subsequent retraction of the needle is less than 2.0 seconds.

In an embodiment, the fluid is one of a hydraulic fluid or a pneumatic fluid.

In an embodiment, a length of the device is between 10 millimeters and 67.5 millimeters. In an embodiment, a height of the device is between 5 millimeters and 16 millimeters. In an embodiment, a width of the device is between 5 millimeters and 27 millimeters.

In an embodiment, the device also includes a clip configured to removably attach the device to one of a person or an item. In an embodiment, the clip includes at least one of a slide-on clip or a pinch clip.

In an embodiment, the device also includes a cartridge sealing ring positioned adjacent to the second end of the cartridge, wherein the fluid is configured to drive the cartridge sealing ring toward the first end of the housing, thereby driving the cartridge toward the first end of the housing.

In an embodiment, the housing is configured to reflect infrared radiation.

In an embodiment, the housing includes a semi-permeable barrier overlaying the penetrable septum. In an embodiment, the semi-permeable barrier comprises flash-spun high-density polyethylene. In an embodiment, the housing is fluid-tight.

In an embodiment, the at least one therapeutic agent is a plurality of therapeutic agents.

In an embodiment, the device also includes at least one sensor.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Unless otherwise defined, all terms (including technical and scientific terms used herein have the same meaning as commonly understood by one having ordinary skill in the art to which this invention belongs. It will further be understood that terms, such as those defined, in commonly used dictionaries, should be interpreted as having a meaning that is consistent with their meaning in the context of the relevant art and the present disclosure and will not be interpreted in an idealized or overly formal sense unless expressly defined.

The present disclosure describes an exemplary embodiment of a miniaturized wearable injection device. It will be apparent to those of skill in the art that the general principles embodied in the exemplary device may also be embodied in other devices. In some embodiments, an exemplary miniaturized wearable injection device is suitable for use as an autoinjector, i.e., a device that is self-administered by a patient who is experiencing an emergency health condition.

Figure 3:
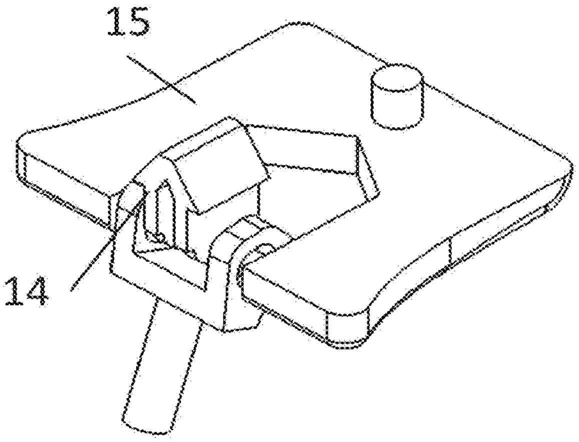
FIG. 3 shows a perspective view of a quick release mount that may interface with the device of FIG. 1.
Figure 4:
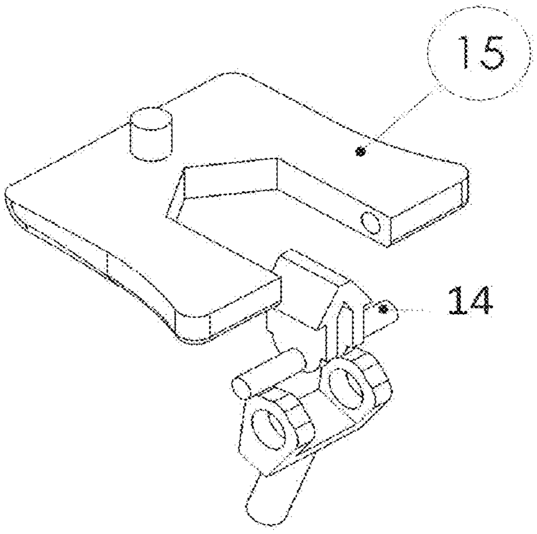
FIG. 4 shows a perspective view of the quick release mount of FIG. 3 and a receiving portion of the device of FIG. 1.

FIG. 1 shows an exploded perspective view of the elements of an exemplary autoinjector 100 (hereinafter the "device 100"). In some embodiments, the device 100 includes a housing 1. In some embodiments, the housing 1 is configured to be removably fastened to a quick release, as shown in FIG. 3. In some embodiments, the quick release is integrated into an accessory, such as a watch band 16. It will be apparent to those of skill in the art that the quick release 13 can be integrated into another item to which a user may wish to affix the device 100 (e.g., another accessory, a bag, a key chain, a backpack, a mobile phone case, a bracelet, a key ring, a bag, a lanyard, a magnet, a mobile phone, a pin, a belt, a carabiner, a backpack clip, a zipper pull, a wallet, a belt clip, etc.). In some embodiments, the quick release includes a housing clip 14 (see FIG. 3) and the housing 1 includes a recess 27 (see FIG. 5) that is sized and shaped to removably receive the housing clip 14. In some embodiments, the quick release includes a pinch clip 15 that is configured such that, when pinched, the pinching force is conveyed to the housing clip 14, thereby allowing the housing clip 14 to be removed from the housing 1 (and, consequently, allowing the device 100 to be removed from the item to which it was attached by the quick release). In some embodiments, the quick release 13 includes a slide-on clip.

In some embodiments, the device 100 includes a cartridge 6 storing a therapeutic agent (e.g., a pharmaceutical). In some embodiments, the cartridge 6 contains 1 mL of the therapeutic agent. In some embodiments, the cartridge 6 contains a mixture including one or more therapeutic agents. In some embodiments, the cartridge has an outside diameter of 9.85 mm. In some embodiments, the cartridge has a length of 35 mm. In some embodiments, the cartridge has a length of 51 mm. In some embodiments, the cartridge has a length of between 46 mm and 56 mm. Examples of therapeutic agents suitable for use in the device 100 include glucagon, insulin, adrenaline, epinephrine, anti-venom, atropine, antibody formulations, antidotes to chemical agents, and the like. In some embodiments, the medication suitable for use in the device of the present invention is at least one medication selected from the group of medications identified by tradenames consisting of Acthar, Actimmune, Apokyn, AquaMephyton, Aranesp, Arixtra, Avonex, Betaseron, Bravelle, Butorphanol, Byetta, Calcijex, Calcitonin, Caverject, Cetrotide, Chorionic Gonadotropin, Cimzia, Copaxone, Copegus, DDAVP, D.H.E-45, Delatestryl, Delestrogen, Depo-Estradiol, Depo-Provera 150, Depo-SubQ Provera 104, Depo-Testosterone, Desmopressin, Dihydroergotamine, Edex, Eligard, Enbrel, Epipen, Epogen, Exjade, Faslodex, Fertinex, Follistim, Forteo, Fragmin, Fuzeon, Ganirelix acetate, Genotropin, Gleevec, Glucagon, Gonal, Heparin, Humatrope, Humira, Imitrex, Increlex, Infergen, Innohep, Insulin, Intron A, iPlex, Ketorolac, Kestrone, Kineret, Kuvan, Leukine, Leuprolide Acetate, Lovenox, Lupron, Luveris, Medroxyprogesterone, Menopur, Methotrexate, Miacalcin, Muse, Neumega, Neulasta, Neupogen, Nexavar, Norditropin, Novarel, Nutropin, NuvaRing, Omnitrope, Orfadin, Ovidrel, Pegasys, Peg-Intron, Pregnyl, Procrit, Profasi, Progesterone, Pulmozyme, Raptiva, Rebetol, Rebif, Repronex, Revlimid, Ribasphere, Ribavirin, Saizen, Sandostatin, Sensipar, Serostim, Somatuline, Sprycel, Somavert, Stadol, Sumatriptan, Supprelin, Sutent, Symlin, Tarceva, Testosterone, Temodar, Tev-Tropin, Thalomid, Tobi, Tykerb, Vitamin B12, Vitamin D, Vitamin K, Xeloda, Zemplar, and Zorbtive. In some embodiments, the device 100 is capable of delivering highly viscous therapeutic agents (e.g., having a viscosity greater than that of water, having a viscosity greater than 30 centipoise, having a viscosity between 30 centipoise and 50 centipoise, etc.), such as biologicals or monoclonal antibodies. It will be apparent to those of skill in the art that the therapeutic agents listed above are only exemplary and that the device 100 is equally suitable for use in connection with practically any other injectable therapeutic agent not specifically listed herein.

In some embodiments, the device 100 is environmentally robust to allow for the device 100 to be worn in a variety of environments while maintaining the stability of the therapeutic agent in the cartridge 6. In some embodiments, the housing 1 is made from a polycarbonate plastic to shield the cartridge 6 from stress and ultraviolet light. In some embodiments, a septum 19 seals a first end of the housing 1. In some embodiments, the housing 1 and the septum 19 are sealed so as to prevent ingress of dust, water, and other contaminants. In some embodiments, the housing 1 provides visibility to the cartridge 6 (e.g., so that the user can read a label). In some embodiments, the housing 1 is at least partially transparent. In some embodiments, the housing 1 has a viewing window providing visibility of the cartridge 6. In some embodiments, a removable cap 17 is provided to cover the viewing window.

In some embodiments, the housing 1 is configured to thermally insulate the therapeutic agent contained within the cartridge 6 from excursions into temperatures that would otherwise cause rapid degradation of the therapeutic agent (e.g., exposure to high levels of heat). In some embodiments, the housing 1 provides for the maintenance of a vacuum on the interior of the housing 1. In some embodiments, the housing 1 includes material insulation. In some embodiments, the housing 1 is formed from a plastic that includes one or more infrared ("IR") reflective additives. In some embodiments, the IR reflective additives include one or more of titanium oxide, bismuth vanadate yellow, chrome antimony titanium buff rutile, chrome iron brown hematite, chrome oxide green, chromium green-black hematite, cobalt aluminate blue spinel, cobalt chromite blue-green spinel, cobalt chromite green spinel, cobalt titanate green spinel, iron manganese black oxide, iron titanium brown spinel, manganese antimony titanium buff rutile, nickel antimony titanium yellow rutile, red iron oxide, ultramarine blue, ultramarine violet, zinc ferrite brown spinel, or another suitable additive. In some embodiments, the one or more IR reflective additives are selected to provide a desired color for the housing 1. In some embodiments, the housing is shielded from stress, heat and radiation via a reflective insulative coating 18.

Figure 2:
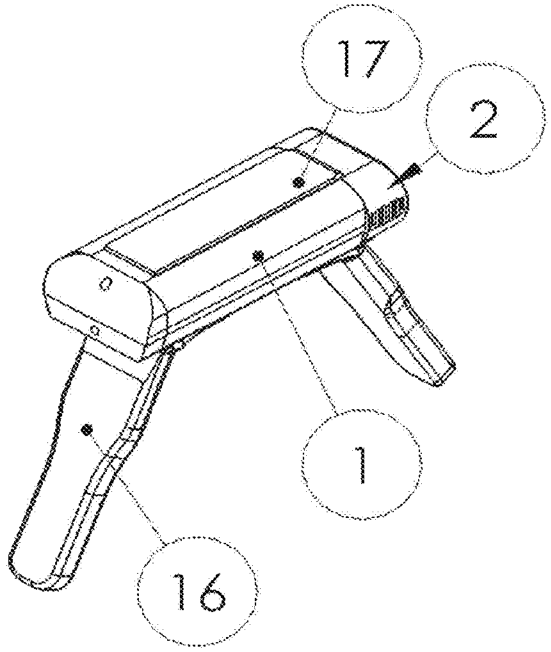
FIG. 2 shows an assembled perspective view of the device of FIG. 1.

In some embodiments, the removable cap 17 provides infrared reflection. In some embodiments, the removable cap 17 is configured to slide off of the housing 1 to reveal the cartridge 6, an indication 20 of the drug temperature, and labeling on the top of the housing 1. In some embodiments, the removable cap 17 is configured to provide the drug with environmental protection and discrete labeling. In some embodiments, the removable cap 17 provides a primary and reversible safety for an activation button 2 that is disposed on the housing 1. In some embodiments, the removable cap 17 is configured to be capable of removal via a thumb push with finger grips as seen in FIG. 2 on the head of the removable cap 17 to allow for a two-finger pinch removal. In some embodiments, the housing 1 and the removable cap 17 are configured such that instructions and labelling are concealed by the removable cap 17 until time of use, when the removable cap 17 is removed. In some embodiments, the device 100 provides voice instructions for use. In some embodiments, the housing 1 includes an integrated information display that is concealed by the removable cap 17. In some embodiments, the device 100 includes a compartment to house pills. In some embodiments, the device 100 includes integrated sensors or other integrated electronics. In some embodiments, the device 100 includes one or more integrated sensors that are configured to sense one or more parameters relating to the device 100 and/or relating to a patient.

In some embodiments, the device 100 includes an activation trigger 2 extending from the housing 1 adjacent to the septum 19. In some embodiments, to activate the device 100, a user removes the removable cap 17 from the housing 1 and presses the housing 1 against an injection site (e.g., against skin or against clothing overlaying the injection site) so as to position the septum 19 at the injection site and press the activation trigger 2 against the skin, thereby triggering administration of the therapeutic agent as will be described hereinafter. In some embodiments, a back plate 3 seals the housing 1 at an end opposite the activation trigger 2. In some embodiments, the cap 17 and the activation trigger 2 provide the device 100 with two safety levels before injection: the cap 17 acts as a primary and reversible safety, while the activation trigger 2 acts as a non-reversible safety. In some embodiments, the cap 17 includes ridged posts that prevent activation of the activation trigger 2 while the cap is in place. In some embodiments, the device 100 includes one or more additional safety mechanisms. In some embodiments, the activation trigger 2 is configured to remain depressed after activation, thereby providing a visual indication that the device 100 has been activated.

In some embodiments, when the activation trigger 2 is pressed, a stored energy system is released. In some embodiments, when the activation trigger 2 is pressed, a deployment spring 11 drives a piston 4 having an O-ring 5. In some embodiments, rather than the deployment spring 11, the device 100 includes a stored energy system that incorporates the release of a pressurized fluid to drive the piston 4 upon activation of the device 100, that incorporates the activation of an electric motor to drive the piston 4 upon activation of the device 100, or that drives the piston 4 in some other manner upon activation of the device 100. In some embodiments, the piston 4 is locked into place by a split lock that engages a portion of the housing 1, and the activation trigger 2 has a conical shape that releases the split lock and allows the piston 4 to move along the housing 1. In some embodiments, the device 100 includes a button spring 21 positioned so as to resist activation of the activation trigger 2, thereby preventing inadvertent activation of the device 100. In some embodiments, once the piston 4 has been unlocked, the deployment spring 11 drives the piston 4 along a first cylinder 23 within the housing 1 in a direction away from the activation trigger 2. In some embodiments, the piston 4 correspondingly drives a fluid (e.g., a hydraulic fluid, a pneumatic fluid, etc.) within the first cylinder 23, through a channel 24 at the end of the housing 1 opposite the activation trigger 2, and along a second cylinder 25, thereby driving a cartridge sealing ring 9, the cartridge 6, and a needle hub 8 toward the septum 19 in a manner so as to provide correct injection depth and volume via a double-ended needle 7 and a rubber plunger 10 as will be described hereinafter. In some embodiments, the fluid is a hydraulic fluid. In some embodiments, the hydraulic fluid includes either glycol, alcohol, or calcium chloride. In some embodiments, the fluid is a pneumatic fluid. In some embodiments, rather than using the deployment spring 11, a stored energy system includes a compressed gas utilizing a valve to control step progress. In some embodiments, the needle hub 8 is crushable (i.e., compressible).

In some embodiments, the needle hub 8 is configured to stabilize the cartridge 6 and align the cartridge 6 and the needle 7 for penetration of the cartridge 6 by the needle 7. In some embodiments, the needle 7 is fixed to the needle hub 8. In some embodiments, the needle 7 is glued to the needle hub 8. In some embodiments, the needle 7 is overmolded into the needle hub 8. In some embodiments, the needle 7 is positioned within a needle sheath 22 prior to deployment of the device 100. In some embodiments, the needle sheath 22 maintains sterility of the needle 7 during assembly of the device 100 and is molded with the needle 7 into the needle hub 8 during assembly of the device 100. In some embodiments, the needle sheath 22 is crushable.

Figure 6:
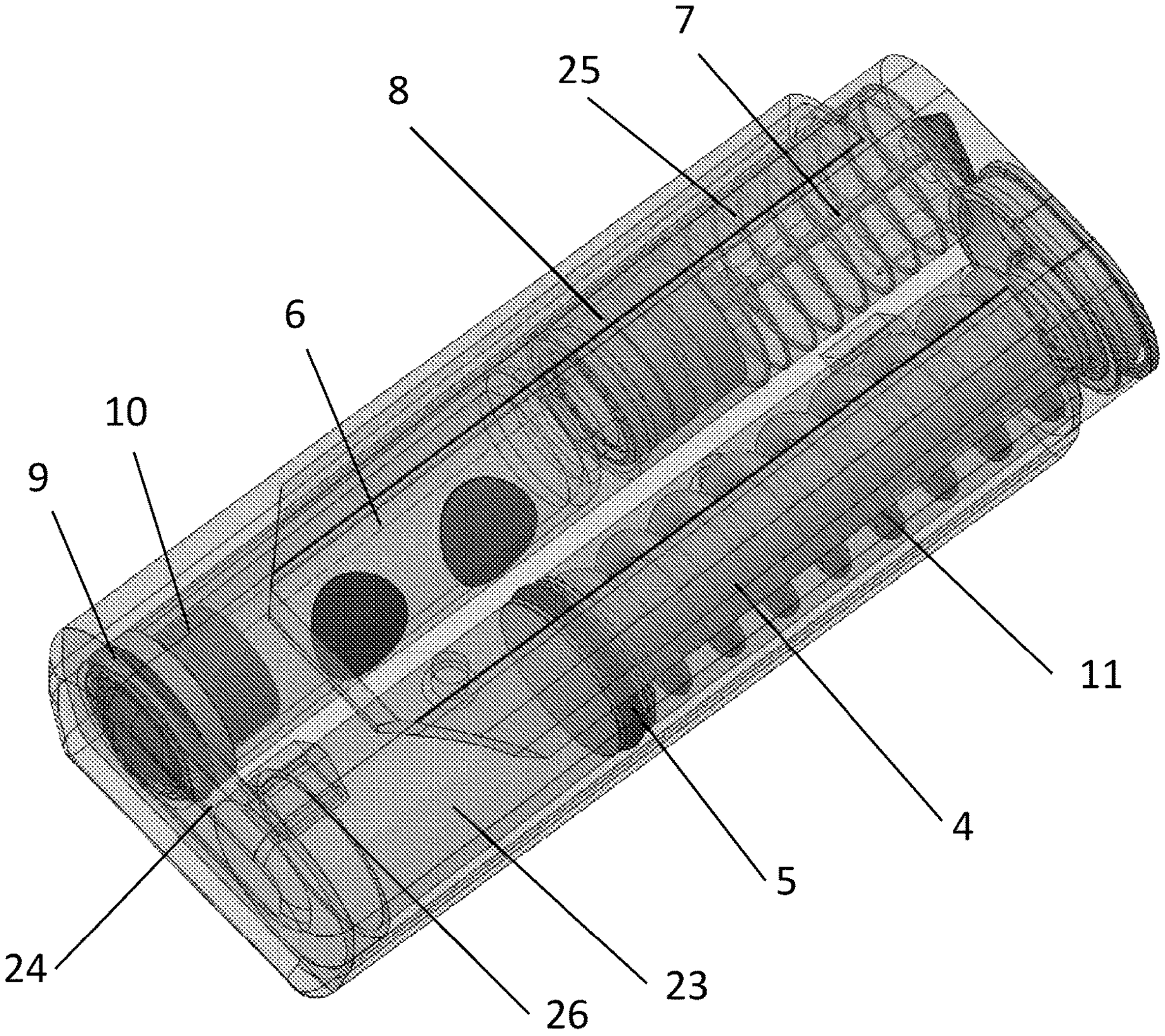
FIG. 6 shows a partially transparent perspective view of the device of FIG. 1 at a time of activation.
Figure 7:
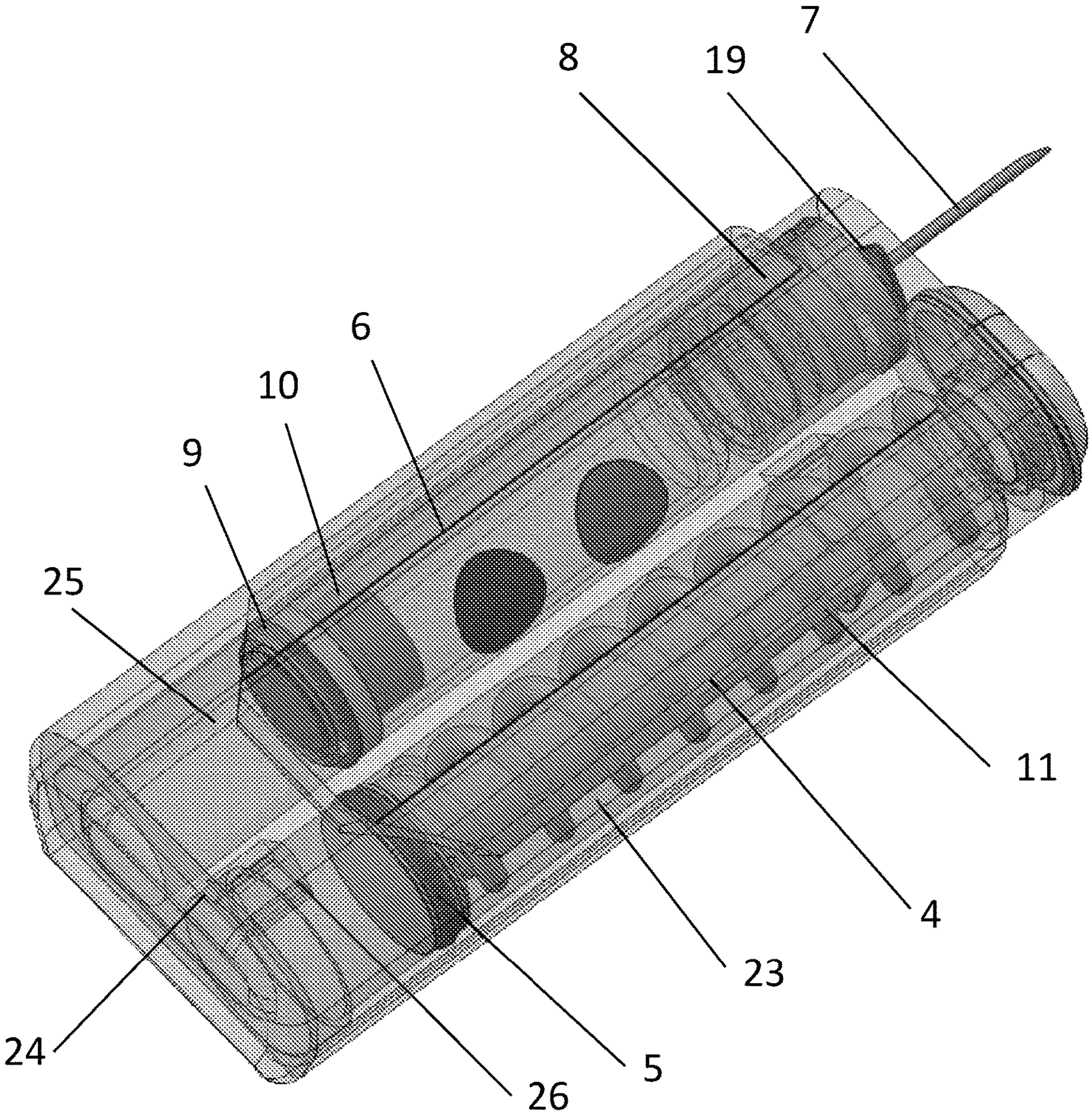
FIG. 7 shows a partially transparent perspective view of the device of FIG. 1 at a first intermediate stage of deployment.

In some embodiments, the piston 4 passes through certain discrete positions as it travels along the first cylinder 23. FIG. 6 shows the device 100 with the activation trigger 2 depressed so as to unlock the piston 4, but prior to the piston 4 traveling along the first cylinder 23. In some embodiments, as the piston 4 travels along the first cylinder 23, it first passes through a first intermediate position, as shown in FIG. 7. In some embodiments, as the piston 4 travels along the first cylinder 23 from the position shown in FIG. 6 to the position shown in FIG. 7, the piston 4 drives the fluid along the first cylinder 23, through the channel 24, and through the second cylinder 25. The movement of the fluid drives the cartridge sealing ring 9, the cartridge 6, the needle hub 8, and the needle 7 toward the septum 19, thereby forcing the needle 7 through the septum 19 and exposing the needle 7. In some embodiments, a sufficient amount of the needle is exposed so as to allow for sufficient injection depth for intramuscular injection. In some embodiments, the amount is at least 10 millimeters. In some embodiments, the amount is at least 12.9 millimeters. In some embodiments, the amount is 12.9 millimeters. In some embodiments, the position shown in FIG. 7 is defined by the needle hub 8 having impacted the housing 1 adjacent to the septum 19.

Figure 8:
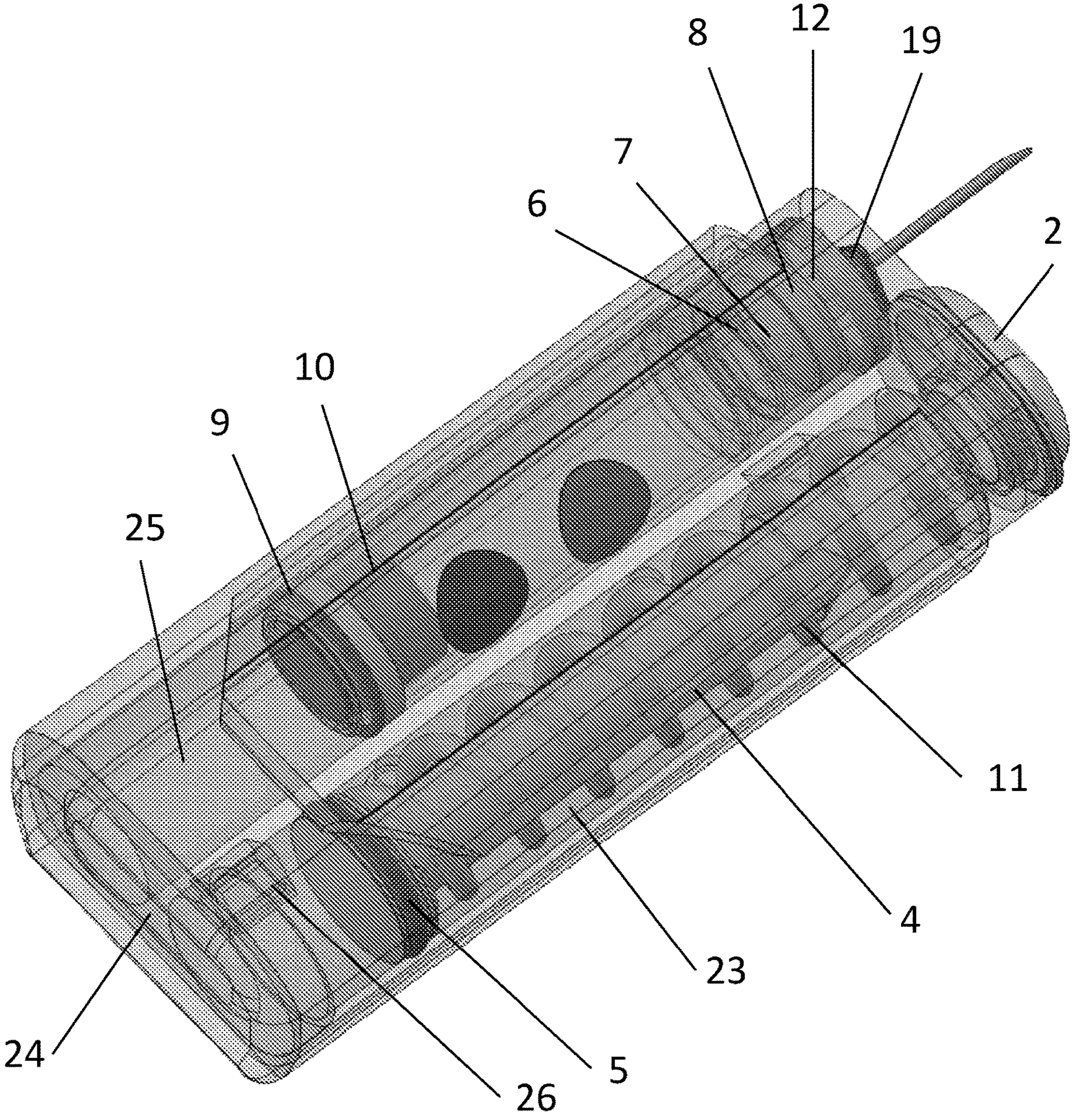
FIG. 8 shows a partially transparent perspective view of the device of FIG. 1 at a second intermediate stage of deployment.

In some embodiments, the piston 4 continues to be forced along the first cylinder 23 by the deployment spring 11, causing motion from the position shown in FIG. 7 to the position shown in FIG. 8. In some embodiments, as the piston 4 travels along the first cylinder 23 from the position shown in FIG. 7 to the position shown in FIG. 8, the piston 4 continues to drive the fluid along the first cylinder 23, through the channel 24, and through the second cylinder 25. In some embodiments, the fluid drives the cartridge sealing ring 9 and the cartridge 6 toward the septum 19, thereby advancing the cartridge 8 within the needle hub 8 and driving the cartridge 6 toward the needle 7, and thereby causing the needle 7 to penetrate the cartridge 6. In some embodiments, the position shown in FIG. 8 is defined by the maximum possible travel of the cartridge 8 within the needle hub 8 under the force provided by the deployment spring 11 and conveyed via the fluid.

Figure 9:
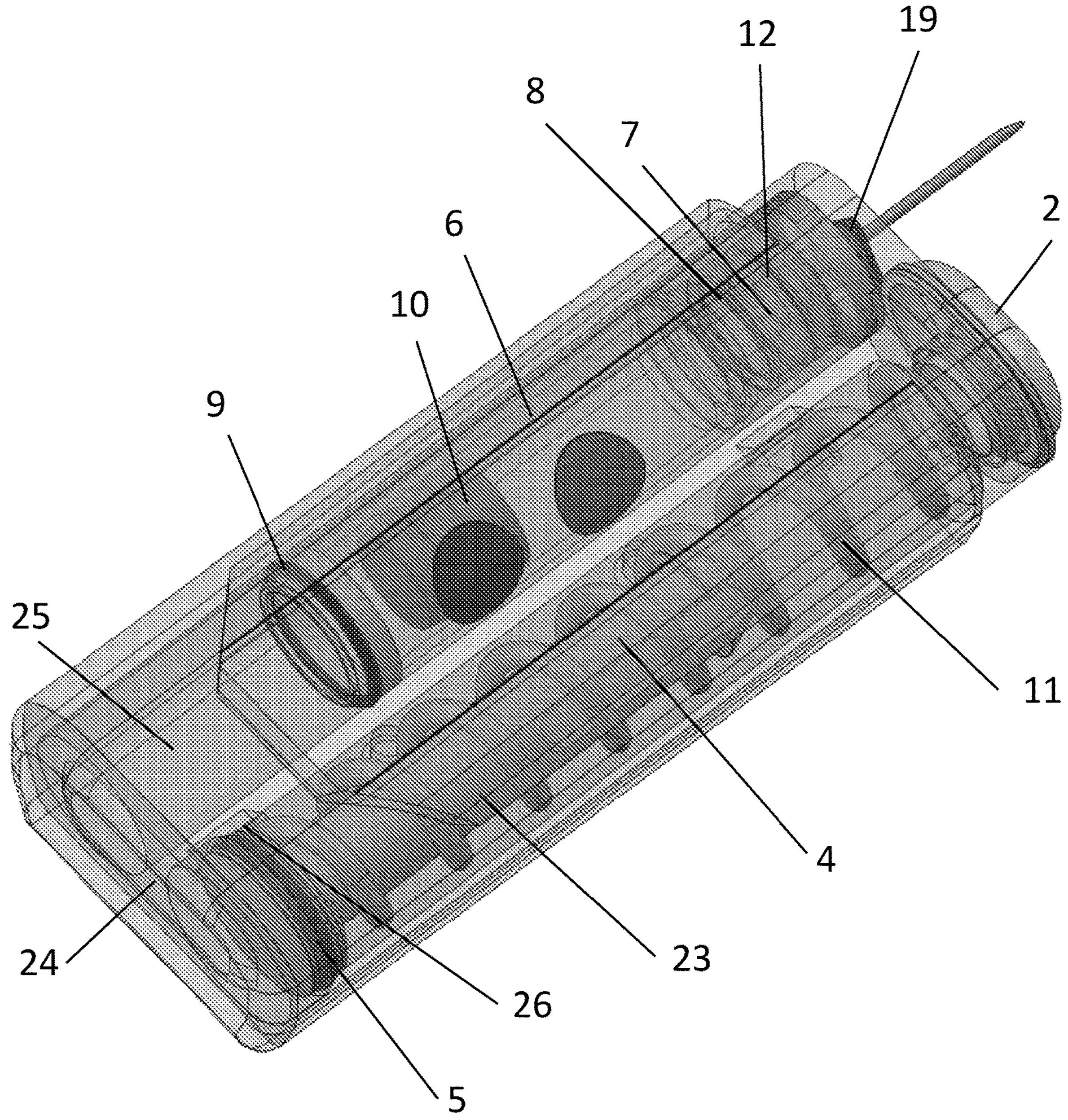
FIG. 9 shows a partially transparent perspective view of the device of FIG. 1 at a third intermediate stage of deployment.

In some embodiments, the piston 4 continues to be forced along the first cylinder 23 by the deployment spring 11, causing motion from the position shown in FIG. 8 to the position shown in FIG. 9. In some embodiments, as the piston 4 travels along the first cylinder 23 from the position shown in FIG. 8 to the position shown in FIG. 9, the piston 4 continues to drive the fluid along the first cylinder 23, through the channel 24, and through the second cylinder 25. In some embodiments, the fluid drives the cartridge sealing ring 9 toward the septum 19. In some embodiments, further movement of the cartridge 6 toward the septum 19 is constrained by the available compression of the needle hub 8. Consequently, in some embodiments, the movement of the cartridge sealing ring 9 toward the septum 19 causes the cartridge sealing ring 9 to drive a plunger 10 of the cartridge 6 toward the septum 19, thereby extruding the therapeutic agent contained within the cartridge 6 through the needle 7.

In some embodiments, continued motion of the piston 4 along the first cylinder 23, as caused by the deployment spring 11, drives the head of the piston 4 to a point such that it passes a pressure relief bore 26 within the first cylinder 23. In some embodiments, the pressure relief bore 26 is a widening (e.g., increase in diameter) of the first cylinder 23 near the end of the housing 1 opposite the activation trigger 2, such that the entire perimeter of the head of the piston 4 is no longer securely engaged with the walls of the first cylinder 23 once the head of the piston 4 has passed the pressure relief bore 26. In some embodiments, the pressure relief bore 26 does not extend entirely about the perimeter of the first cylinder 23. In some embodiments, once the O-ring 5 of the piston 4 has passed the relief ring, motion of the piston 4 no longer drives the fluid, but, rather, the fluid is permitted to travel behind the head of the piston 4 and along the first cylinder 23 toward the activation trigger 2. In some embodiments, once the piston 4 no longer drives the fluid, the pressure on the plunger 10 described in the previous paragraph is relieved, and the therapeutic agent ceases to be extruded through the needle 7. In some embodiments, the piston 4 continues to drive the fluid through the channel 24, thereby driving the plunger 10 and extruding the therapeutic agent through the needle 7, until the piston 4 has passed the pressure relief bore 26. Consequently, in some embodiments, the location of the pressure relief bore 26 may be configured to control an amount of the therapeutic agent that is extruded through the needle 7. FIG. 9 shows the piston 4 positioned past the pressure relief bore 26, allowing the fluid to flow into the first cylinder 23 behind the piston 4. Consequently, FIG. 9 shows the plunger 10 at its maximum depth within the cartridge 6, i.e., an entire dose of the therapeutic agent has been administered. In some embodiments, the dosage amount is between 100 uM and 0.7 mL.

Figure 10:
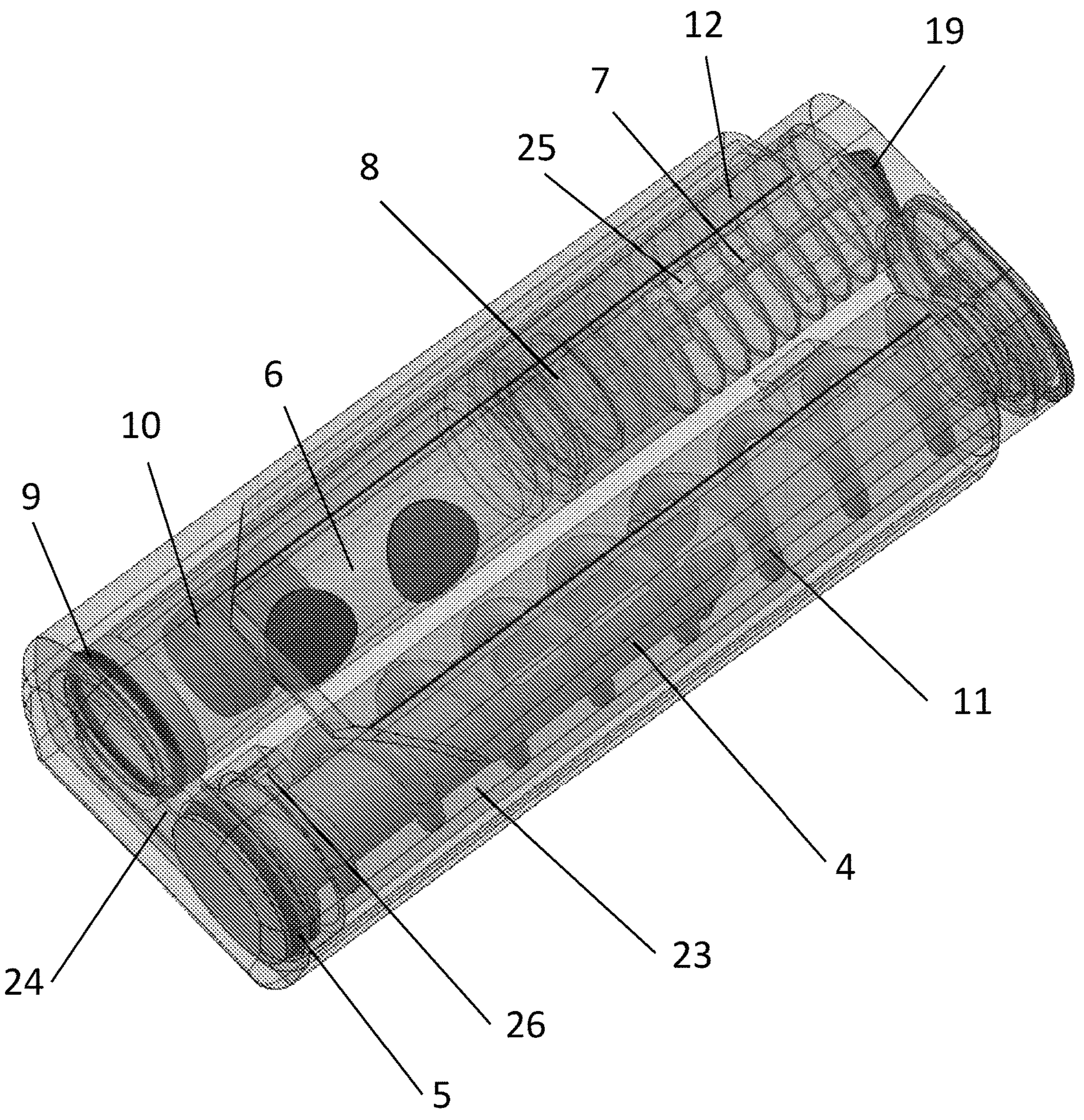
FIG. 10 shows a partially transparent perspective view of the device of FIG. 1 after deployment has been completed.

As noted above, in some embodiments, once the piston 4 has passed the pressure relief bore 26 and the fluid is permitted to flow behind the piston 4 into the first cylinder, the piston 4 will no longer drive the fluid through the channel 24 and along the second cylinder 25 to apply pressure to the cartridge sealing ring 9. Once pressure applied by the fluid has abated, a retraction spring 12 forces the needle hub 8, the cartridge 6, the cartridge sealing ring 9, and the needle 7 away from the septum 19 of the housing 1, thereby retracting the needle to a position that is entirely within the housing 1. In some embodiments, the retraction spring 12 is selected so as to be strong enough to provide an immediate or near-immediate retraction of the needle 7 once the pressure has abated, but not so strong as to prevent the cartridge 6 and associated elements from advancing toward the septum 19 while the pressure is being applied by the deployment spring 11 and the piston 4. FIG. 10 shows the device 100 after the retraction spring 12 has retracted the cartridge 6 and other elements, thereby retracting the needle 7 within the housing 1.

In some embodiments, the deployment spring 11 and the retraction spring 12 are configured (e.g., selected to have an appropriate spring coefficient) such that the entire process of activation, deployment, administration of the therapeutic agent, and retraction is performed within a predefined period of elapsed time. In some embodiments, the predefined period of elapsed time is selected in order to be a clinically acceptable time period. In some embodiments, the period of elapsed time is less than 2.0 seconds. In some embodiments, the period of elapsed time is less than 1.5 seconds. In some embodiments, the period of elapsed time is less than 1.0 seconds. In some embodiments, the period of elapsed time is less than 0.5 seconds. In some embodiments, the period of elapsed time is between 0.2 seconds and 2.0 seconds. In some embodiments, the period of elapsed time is between 0.2 seconds and 1.5 seconds. In some embodiments, the period of elapsed time is between 0.2 seconds and 1.0 seconds. In some embodiments, the period of elapsed time is between 0.2 seconds and 0.5 seconds. In some embodiments, the period of elapsed time is between 0.5 seconds and 2.0 seconds. In some embodiments, the period of elapsed time is between 0.5 seconds and 1.5 seconds. In some embodiments, the period of elapsed time is between 0.5 seconds and 1.0 seconds. In some embodiments, the period of elapsed time is between 1.0 seconds and 2.0 seconds. In some embodiments, the period of elapsed time is between 1.0 seconds and 1.5 seconds. In some embodiments, the period of elapsed time is between 1.5 seconds and 2.0 seconds.

In some embodiments, the device 100 also includes a semi-permeable barrier 28 positioned adjacent to the septum 19. In some embodiments, the semi-permeable barrier 28 includes polyethylene. In some embodiments, the semi-permeable barrier 28 includes flash-spun high-density polyethylene ("HDPE"). In some embodiments, the semi-permeable barrier 28 includes flash-spun HDPE of the type commercialized by DuPont de Nemours, Inc. of Wilmington Del. under the trade name TYVEK. In some embodiments, the semi-permeable barrier 28 can be penetrated by the needle 7 but is not permeable to water, thereby rendering the assembled device 100 waterproof. In some embodiments, the semi-permeable barrier 28 does not absorb moisture and the housing 1 of the device 100 is otherwise fluid-tight, thereby enabling the assembled device 100 to be sterilized using ethylene oxide sterilization or another liquid-based or gas-based sterilization technique.

Figure 11:
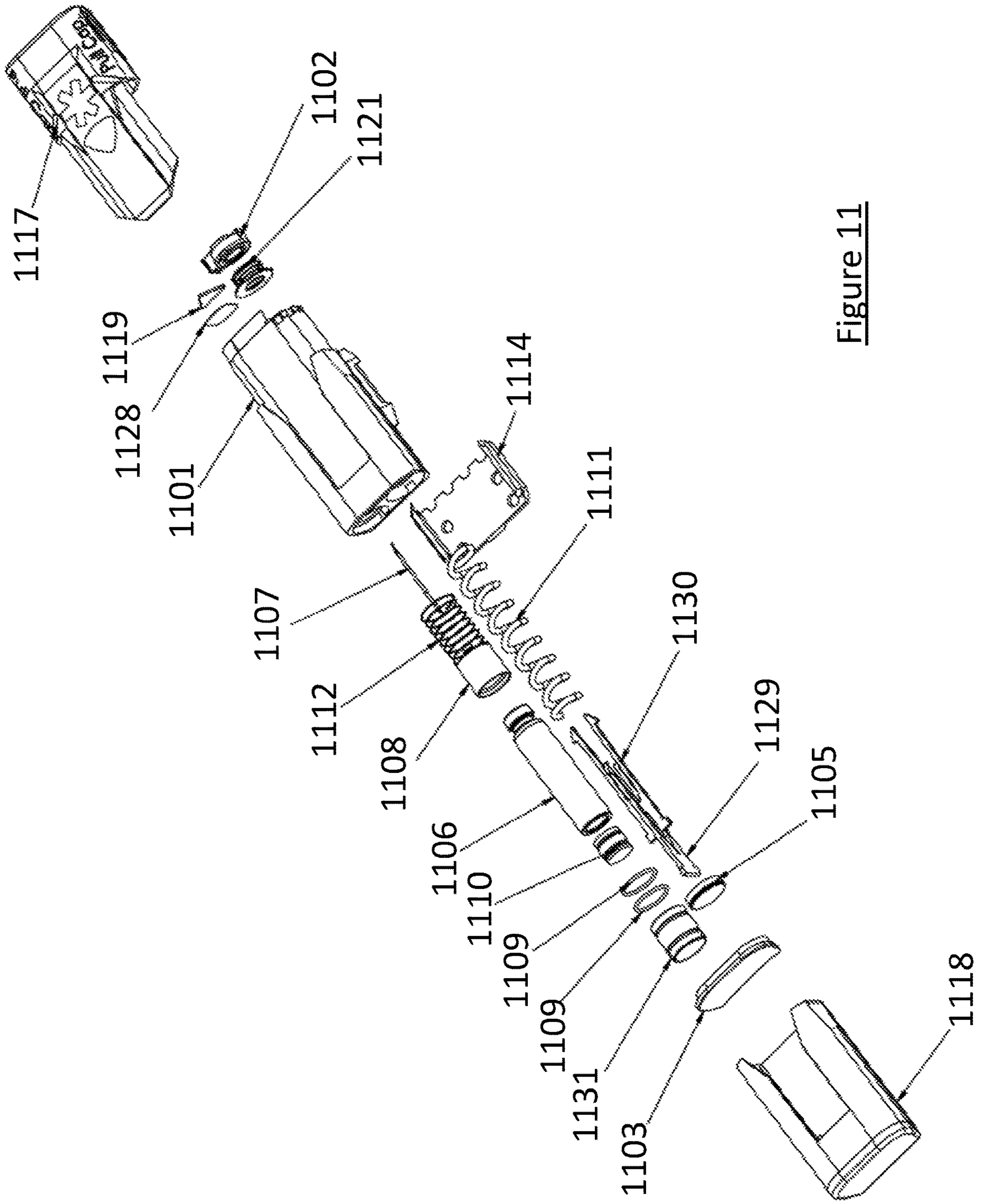
FIG. 11 shows an exploded perspective view of an exemplary miniaturized wearable medication administration device.

FIG. 11 shows an exploded view of an exemplary device 1100. In some embodiments, the device 1100 is substantially similar to the device 100 discussed above other than as will be discussed in further detail hereinafter. In some embodiments, the device 1100 includes a housing 1101 having a first end and a second end. In some embodiments, the device 1100 includes an activation trigger 1102 positioned at the first end of the housing 1101. In some embodiments, the device 1100 includes a back plate 1103 sealing the housing 1101 at the second end of the housing 1101. In some embodiments, the device 1100 includes a two-piece piston including a first piston element 1129 and a second piston element 1130. In some embodiments, the piston includes an O-ring 1105. In some embodiments, the device 1100 includes a cartridge 1106. In some embodiments, the device 1100 includes a syringe 1107. In some embodiments, the device 1100 includes a needle hub 1108. In some embodiments, the device 1100 includes a cartridge sealing ring 1131. In some embodiments, the cartridge sealing ring 1131 carries one or more cartridge sealing O-rings 1109. In some embodiments, the cartridge sealing ring 1131 carries two of the O-rings 1109. In some embodiments, the device 1100 includes a plunger 1110. In some embodiments, the device 1100 includes a deployment spring 1111. In some embodiments, the device 1100 includes a retraction spring 1112. In some embodiments, the device 1100 includes a slide plate 1114. In some embodiments, the slide plate 1114 is configured to removably attach to the housing 1101 (e.g., by sliding onto and off of the housing 1101). In some embodiments, the device 1100 includes a removable cap 1117. In some embodiments, the device 1100 includes an insulative coating 1118. In some embodiments, the device 1100 includes a septum 1119. In some embodiments, the device 1100 includes a button spring 1121 positioned between the activation trigger 1102 and the two-piece piston and configured to facilitate deployment of the two-piece piston. In some embodiments, the device 1100 includes a semi-permeable barrier 1128.

Figure 12:
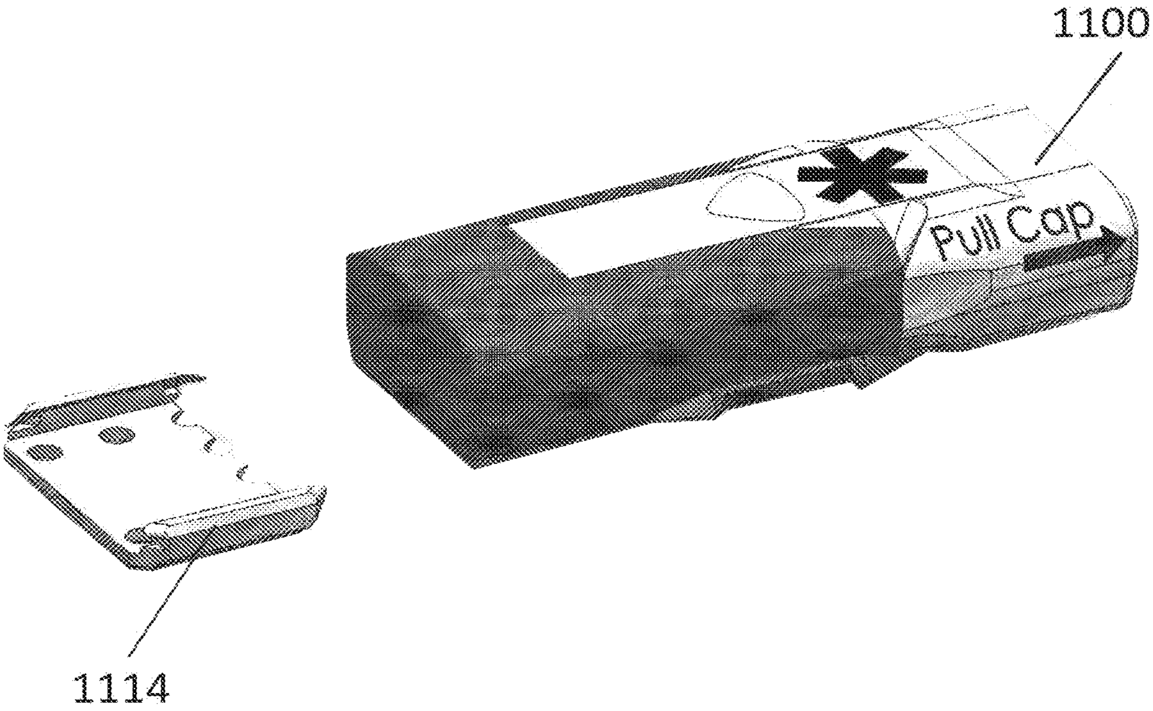
FIG. 12 shows a top perspective view of the exemplary miniaturized wearable medication administration device of FIG. 11 with a slide plate removed therefrom.
Figure 13:
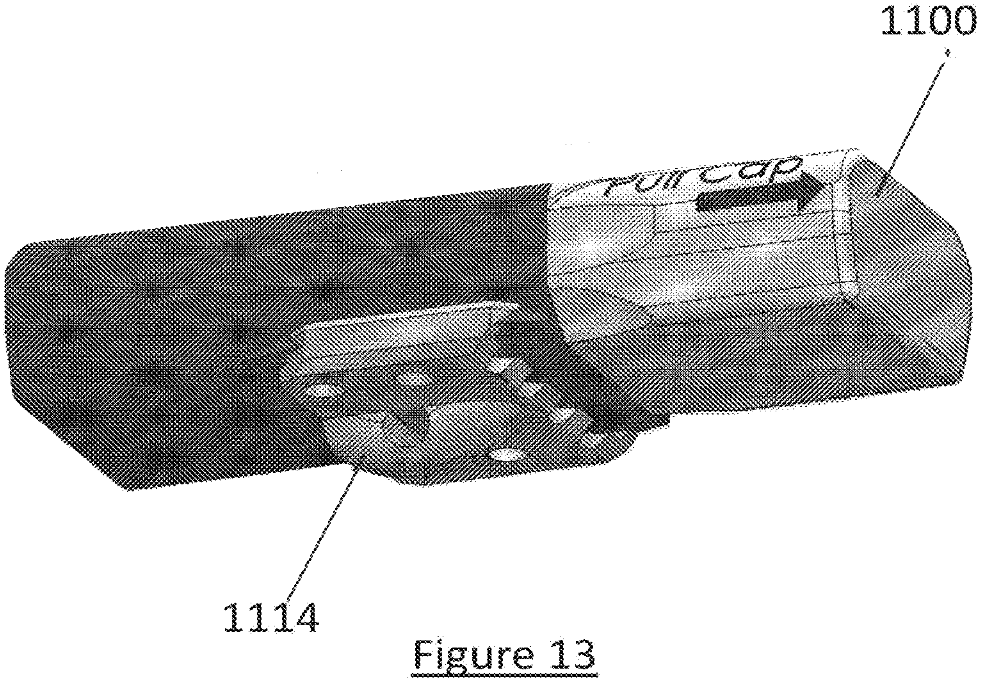
FIG. 13 shows a bottom perspective view of the exemplary miniaturized wearable medication administration device of FIG. 11 with a slide plate attached thereto.

FIG. 12 shows a top perspective view of the device 1100 with the slide plate 1114 removed therefrom. FIG. 13 shows a bottom perspective view of the device 1100 with the slide plate 1114 attached thereto.

In some embodiments, a medication administration device as described herein (e.g., the device 100 or the device 1100) may be provided as a miniaturized wearable medication administration device. In some embodiments, a miniaturized wearable medication administration device having a quick release as described above can be of a size that is small enough to be conveniently attached to a user's person (e.g., clipped to a user's clothes) or coupled to another item (e.g., another accessory, a bag, a key chain, a backpack, a mobile phone case, a bracelet, a key ring, a bag, a lanyard, a magnet, a mobile phone, a pin, a belt, a carabiner, a backpack clip, a zipper pull, a wallet, a belt clip, etc.) for ease of carrying, transportation, and access, but is still sufficiently large so as to be easily held and manipulated by a user.

In some embodiments, a medication administration device as described herein (e.g., the device 100 or the device 1100) is configured for into a jewelry or wearable accessory that is adaptable to a wide variety of styles. In some embodiments, such a device includes one to two attachment sites through pins or clips that are compatible with the device and provide multiple functionalities. In some embodiments, the first site has a bail that effectively turns the device into a pendant or any accessory that is desired. In some embodiments, the second pin has a hinge knuckle onto which other parts (e.g., a cover, a second bail, a charm, etc.) can attach. In some embodiments, when a cover is used, the first pin has the additional functionality of being an attachment point for closure. In some embodiments, both attachment maximize unintentional interference with the device and support the device from opposing and/or pulling forces with minimal wear. In some embodiments, the attachment points work in harmony to transform the device into any wearable jewelry the user desires. In some embodiments, the attachment points also permit connection to other personal accessories or clothing such as cellphones or backpacks or belts.

In some embodiments, a medication administration device as described herein (e.g., the device 100 or the device 1100) has an activation trigger and a syringe located adjacent to one another at the same end of the device, and is activated by pressing the end of the device having the activation trigger against the skin of the patient at an appropriate location for administration of a therapeutic agent (e.g., the thigh). Consequently, in some embodiments, such a medication administration device can allow for administration of a therapeutic agent with a minimal amount of effort, and is suitable for use as an autoinjector (i.e., a device that is self-administered by a patient).

In some embodiments, an exemplary miniaturized wearable medication administration device (e.g., the device 100 described above) has a length (e.g., as measured between the outward-facing end of the removable cap 17 and the opposing outward-facing end of the coating 18) that is in a range of between 61.5 mm and 67.5 mm. In some embodiments, the length is between 62 mm and 67 mm. In some embodiments, the length is between 62.5 mm and 66.5 mm. In some embodiments, the length is between 63 mm and 66 mm. In some embodiments, the length is between 63.5 mm and 65.5 mm. In some embodiments, the length is between 64 mm and 65 mm. In some embodiments, the length is about 61.5 mm. In some embodiments, the length is 61.5 mm. In some embodiments, the length is about 62 mm. In some embodiments, the length is 62 mm. In some embodiments, the length is about 62.5 mm. In some embodiments, the length is 62.5 mm. In some embodiments, the length is about 63 mm. In some embodiments, the length is 63 mm. In some embodiments, the length is about 63.5 mm. In some embodiments, the length is 63.5 mm. In some embodiments, the length is about 64 mm. In some embodiments, the length is 64 mm. In some embodiments, the length is about 64.5 mm. In some embodiments, the length is 64.5 mm. In some embodiments, the length is about 65 mm. In some embodiments, the length is 65 mm. In some embodiments, the length is about 65.5 mm. In some embodiments, the length is 65.5 mm. In some embodiments, the length is about 66 mm. In some embodiments, the length is 66 mm. In some embodiments, the length is about 66.5 mm. In some embodiments, the length is 66.5 mm. In some embodiments, the length is about 67 mm. In some embodiments, the length is 67 mm. In some embodiments, the length is about 67.5 mm. In some embodiments, the length is 67.5 mm. In some embodiments, the length is less than 67.5 mm. In some embodiments, the length is between 10 mm and 67.5 mm.

Figure 5:
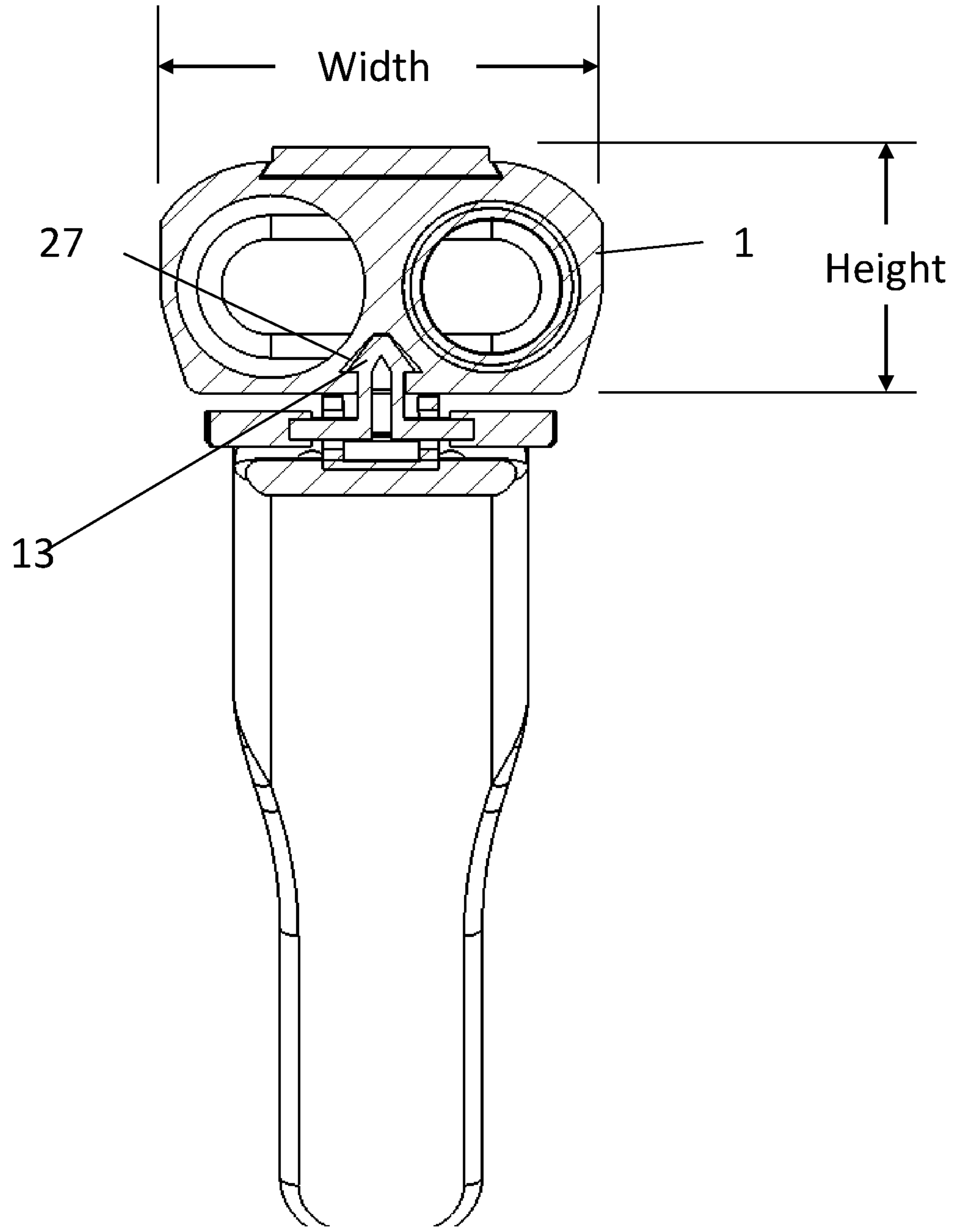
FIG. 5 shows a cross-sectional view of the device of FIG. 1 and a garment incorporating the quick release mount of FIG. 3.

In some embodiments, an exemplary miniaturized wearable medication administration device (e.g., the device 100 described above) has a width (e.g., as measured between opposing sides of the housing 1, as shown in FIG. 5) that is in a range of between 23.6 mm and 27.6 mm. In some embodiments, the width is between 24.1 mm and 27.1 mm.

In some embodiments, the width is between 24.6 mm and 26.6 mm. In some embodiments, the width is between 25.1 mm and 26.1 mm. In some embodiments, the width is about 23.1 mm. In some embodiments, the width is 23.1 mm. In some embodiments, the width is about 23.6 mm. In some embodiments, the width is 23.6 mm. In some embodiments, the width is about 24.1 mm. In some embodiments, the width is 24.1 mm. In some embodiments, the width is about 24.6 mm. In some embodiments, the width is 24.6 mm. In some embodiments, the width is about 25.1 mm. In some embodiments, the width is 25.1 mm. In some embodiments, the width is about 25.6 mm. In some embodiments, the width is 25.6 mm. In some embodiments, the width is about 26.1 mm. In some embodiments, the width is 26.1 mm. In some embodiments, the width is about 26.6 mm. In some embodiments, the width is 26.6 mm. In some embodiments, the width is about 27.1 mm. In some embodiments, the width is 27.1 mm. In some embodiments, the width is about 27.6 mm. In some embodiments, the width is 27.6 mm. In some embodiments, the width is about 24 mm. In some embodiments, the width is 24 mm. In some embodiments, the width is about 25 mm. In some embodiments, the width is 25 mm. In some embodiments, the width is about 26 mm. In some embodiments, the width is 26 mm. In some embodiments, the width is about 27 mm. In some embodiments, the width is 27 mm. In some embodiments, the width is less than 27 mm. In some embodiments, the width is between 5 mm and 27 mm.

In some embodiments, an exemplary miniaturized wearable medication administration device (e.g., the device 100 described above) has a height (e.g., as measured between the opposing top and bottom of the housing 1, as shown in FIG. 5) that is in a range of between 12.6 mm and 16.6 mm. In some embodiments, the height is between 13.1 mm and 16.1 mm. In some embodiments, the height is between 13.6 mm and 15.6 mm. In some embodiments, the height is between 14.1 mm and 15.1 mm. In some embodiments, the height is about 12.6 mm. In some embodiments, the height is 12.6 mm. In some embodiments, the height is about 13.1 mm. In some embodiments, the height is 13.1 mm. In some embodiments, the height is about 13.6 mm. In some embodiments, the height is 13.6 mm. In some embodiments, the height is about 14.1 mm. In some embodiments, the height is 14.1 mm. In some embodiments, the height is about 14.6 mm. In some embodiments, the height is 14.6 mm. In some embodiments, the height is about 15.1 mm. In some embodiments, the height is 15.1 mm. In some embodiments, the height is about 15.6 mm. In some embodiments, the height is 15.6 mm. In some embodiments, the height is about 16.1 mm. In some embodiments, the height is 16.1 mm. In some embodiments, the height is about 16.6 mm. In some embodiments, the height is 16.6 mm. In some embodiments, the height is about 13 mm. In some embodiments, the height is 13 mm. In some embodiments, the height is about 14 mm. In some embodiments, the height is 14 mm. In some embodiments, the height is about 15 mm. In some embodiments, the height is 15 mm. In some embodiments, the height is about 16 mm. In some embodiments, the height is 16 mm. In some embodiments, the height is less than 16 mm. In some embodiments, the height is between 5 mm and 16 mm.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A device, comprising:
- a housing having a first end, a second end, a first section extending from the first end to the second end, a second section to the first section, and a channel connecting the first section to the second section proximate to the second end;
- a stored energy system configured to deliver pressurized fluid, the fluid including a hydraulic fluid, the stored energy system including:
  - a piston slidably positioned within the first section adjacent to a volume of fluid contained in the first section; and
  - a deployment spring disposed in the first section and configured to move the piston toward the second end of the housing such that the volume of fluid contained in the first section is driven through the channel and into the second section;
- a penetrable septum configured to separate an interior of the housing from an external environment surrounding the housing;
- a cartridge having a first end and a second end, wherein the cartridge contains at least one therapeutic agent, wherein the cartridge has a plunger disposable at the second end of the cartridge and movable within the cartridge toward the first end of the cartridge, wherein the cartridge is slidably positioned within the second section such that the second end of the cartridge faces the second end of the housing;
- a cartridge sealing ring positioned directly adjacent to and in contact with the second end of the cartridge, wherein the volume of fluid is configured to drive movement of the cartridge sealing ring toward the first end of the housing to drive the movement of cartridge toward the first end of the housing;
- a dual-ended needle positioned between the cartridge and the septum; and
- an activation trigger configured to be actuated to release the piston and the deployment spring to drive the volume of fluid from the first section to the second section to drive:
  - movement of the cartridge and the needle toward the septum such that the needle penetrates the septum and inserts into skin adjacent to the septum;
  - movement of the cartridge toward the needle such that the needle penetrates the first end of the cartridge; and
  - movement of the plunger within the cartridge to force at least a portion of the at least one therapeutic agent to extrude through the needle and into the skin.

2. The device of claim 1, further comprising a retraction spring positioned within the second section, wherein the retraction spring is configured to retract the needle toward the second end of the housing after the volume of fluid stops driving the movement of the plunger to position the needle entirely within the housing.

3. The device of claim 2, wherein the piston includes a sealing element, wherein the first section includes a relief bore positioned proximate to the second end of the housing, wherein the relief bore is configured such that, when the sealing element is positioned between the relief bore and the second end of the housing, the volume of fluid is permitted to flow into a portion of the first section between the sealing element and the first end of the housing, thereby removing pressure from the cartridge and stopping the volume of fluid from driving the movement of the plunger.

4. The device of claim 3, wherein a position of the relief bore is configured so as to control an amount of the at least one therapeutic agent to be extruded through the needle.

5. The device of claim 3, wherein the deployment spring and the retraction spring are configured such that an elapsed time between an actuation of the activation trigger and a subsequent retraction of the needle is less than 2.0 seconds.

6. The device of claim 1, wherein a length of the device is between 10 millimeters and 67.5 millimeters.

7. The device of claim 1, wherein a height of the device is between 5 millimeters and 16 millimeters.

8. The device of claim 1, further comprising a clip configured to removably attach the device to at least one of a person or an item.

9. The device of claim 8, wherein the clip includes at least one of a slide-on clip or a pinch clip.

10. The device of claim 1, wherein the housing is configured to reflect infrared radiation.

11. The device of claim 1, wherein the housing includes a semi-permeable barrier overlaying the penetrable septum.

12. The device of claim 11, wherein the semi-permeable barrier comprises flash-spun high-density polyethylene.

13. The device of claim 11, wherein the housing is fluid-tight.

14. The device of claim 1, wherein the at least one therapeutic agent is a plurality of therapeutic agents.

15. The device of claim 1, further comprising at least one sensor.

16. The device of claim 1, wherein the activation trigger is configured to be actuated to release the piston and the deployment spring to drive the volume of fluid from the first section to the second section to drive the movement of the cartridge and the needle toward the septum, followed by the movement of the cartridge toward the needle, and further followed by the movement of the plunger within the cartridge, such that the needle is inserted into the skin and is disposed in the cartridge prior to the at least one therapeutic agent being extruded through the needle.

17. The device of claim 1, wherein the activation trigger is disposed on the first end of the housing and the needle is configured to penetrate through the septum on the first end of the housing, the activation trigger configured to be actuated when the first end of the housing is pressed against the skin.

18. The device of claim 1, wherein the second section is disposed parallel to the first section.

19. The device of claim 1, wherein the activation trigger is disposed on a longitudinal axis of the first section.

20. The device of claim 1, wherein a longitudinal axis of the activation trigger is perpendicular with a longitudinal axis of the dual-ended needle.

* * * * *